United States Patent [19]

Heiba et al.

[11] 4,081,456
[45] Mar. 28, 1978

[54] BIS-LACTAM DERIVATIVES

[75] Inventors: El Ahmadi I. Heiba, Princeton; Ralph M. Dessau, Edison Township, Middlesex County, both of N.J.

[73] Assignee: Mobil Oil Corporation, New York, N.Y.

[21] Appl. No.: 659,803

[22] Filed: Feb. 20, 1976

Related U.S. Application Data

[63] Continuation of Ser. No. 336,564, Feb. 28, 1973, abandoned, which is a continuation-in-part of Ser. No. 799,939, Feb. 17, 1969, abandoned, which is a continuation-in-part of Ser. No. 714,447, Mar. 20, 1968, abandoned.

[51] Int. Cl.² ............... C07D 403/06; C07D 403/12
[52] U.S. Cl. .............. 260/326.25; 260/326.5 FC; 260/343.6; 252/51.5 R; 252/52 R; 44/63
[58] Field of Search ............ 260/326.25, 343.6

[56] References Cited

U.S. PATENT DOCUMENTS

| | | | |
|---|---|---|---|
| 2,578,526 | 12/1951 | Evans | 260/326.25 |
| 2,993,021 | 7/1961 | Bavley et al. | 260/326.25 |
| 3,200,075 | 8/1965 | Anderson | 260/343.6 |
| 3,261,782 | 7/1966 | Anderson et al. | 260/343.6 |
| 3,341,542 | 9/1967 | Le Suer et al. | 260/326.25 |
| 3,444,185 | 5/1969 | Nau | 260/326.25 |
| 3,459,738 | 8/1969 | Morren | 260/326.25 |
| 3,487,452 | 12/1969 | Wygant et al. | 260/343.6 |
| 3,520,902 | 7/1970 | Anderson | 260/326.25 |
| 3,549,654 | 12/1970 | Collins | 260/326.25 |
| 3,579,536 | 5/1971 | Vail et al. | 260/326.25 |
| 3,708,473 | 1/1973 | Collins | 260/326.25 |
| 3,925,411 | 12/1975 | Dahlbom | 260/326.25 |

*Primary Examiner*—Donald G. Daus
*Assistant Examiner*—Mary Vaughn
*Attorney, Agent, or Firm*—Charles A. Huggett; Vincent J. Frilette

[57] ABSTRACT

Gamma-alkyl-gamma-butyrolactones having an alkyl substituent of at least 16 carbon atoms in length, preferably at least 25 carbon atoms, are formed by reacting a monoolefin with a carboxylic acid in the presence of a reducible metal ion of higher-valent form, such as the manganic ion, $Mn^{+3}$. The resulting lactones are useful as antiwear agents and for improving the adherence of wax coatings of paper and, upon reaction with amines, polyalkylenepolyamines, for providing novel lactams and bislactams useful as multifunctional agents in lubricants, fuels, coolants and other organic fluids. Thus, the compounds of this invention are of the general structure

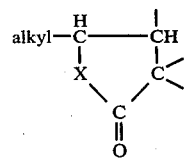

the alkyl group being as defined above, X being oxygen, imino, alkylimino, polyalkylenepolyamino or lactam(-polyalkylenepolyamino) and the dangling valences being hydrogen or lower alkyl (that is, no greater than 6 carbon atoms).

10 Claims, No Drawings

BIS-LACTAM DERIVATIVES

CROSS-REFERENCE TO RELATED APPLICATIONS

This application is a continuation of copending application Ser. No. 336,564 filed Feb. 28, 1973, now abandoned which is a continuation-in-part of application Ser. No. 799,939, filed on Feb. 17, 1969, now abandoned which is a continuation-in-part of application Ser. No. 714,447, filed Mar. 20, 1968, now abandoned. Copending application Ser. No. 176,267, a continuation-in-part of application Ser. No. 799,939 is now U.S. Pat. No. 3,734,865.

BACKGROUND OF THE INVENTION

1. Field of the Invention

This invention relates to novel gamma-substituted gamma-butyrolactones, and in particular it relates to gamma-alkyl lactams having at least 16 carbon atoms in the alkyl substituent and to amine derivatives thereof.

2. Description of the Prior Art

In U.S. Pat. No. 2,296,709 of Fernholz there is disclosed gamma-butyrolactones made by the oxidation of alphatocopherol, not by the reaction of an olefin with a carboxylic acid. In U.S. Pat. Nos. 3,200,075 of Anderson and 3,261,782 of Anderson et al., the lactones disclosed contain an amido or a carboxyl substituent on the ring adjacent to the carbonyl carbon atom. The substituent attached to the carbon atom adjacent to the ring oxygen may contain from 1 to 300 carbon atoms. In U.S. Pat. No. 3,487,452 of Wygant et al, the lactones disclosed also contain the alphaamido substituent and an alkyl substituent of up to 20 carbon atoms. These patents fail to disclose specific gamma-alkyl-substituted butyrolactones derived from olefins having a chain length of at least 16 carbon atoms and carboxylic acids, or their alkylenepolyamine derivatives or the utility of the lactone as a wax coating adherent or the utility of the lactones or the amine derivatives as multifunctional agents in industrial organic fluids.

SUMMARY OF THE INVENTION

In accordance with the present invention, there are provided novel substituted gamma-butyrolactones and gamma-butyrolactams having the formula

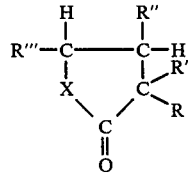

wherein X is oxygen, imino, alkylimino, or an imino linkage derived from a polyalkylenepolyamine or a lactam(polyalkylenepolyamine); wherein R and R' are individually hydrogen or alkyl of from 1 to 5 carbon atoms, and each may be the same or different; R" is hydrogen or alkyl of 1 to 3 carbon atoms; and R'" is an alkyl group containing at least 16 carbon atoms in length, preferably a total of at least 25, and more preferably from 25 to about 100 carbon atoms. When X is an imino, the compound is a lactam or a bis-lactam. Preferably X is derived from a polyalkylenepolyamine:

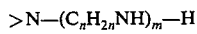

or

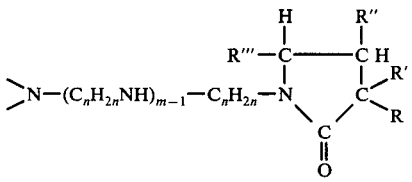

wherein $n$ is an integer of 2 to 4 and $m$ is an integer of 1 to 10.

DESCRIPTION OF SPECIFIC EMBODIMENTS

The lactones represented by the general formula shown above can be prepared by the process described in application Ser. No. 714,447 now abandoned in favor of continuation-in-part application Ser. No. 799,939. The olefinic reactant is a 1- to 4-monoolefin having at least 16 carbon atoms in a straight chain and preferably at a total of 25 to 100 carbon atoms per molecule.

Typical of such olefins are: 1-hexadecene, 1-heptadecene, 1-octadecene, 1-eiocosene, 1-pentacosene; 1-hexacosene, 1-heptacosene; 1-octacosene; 1-triacontene and polymers of short chain olefins such as ethylene, propylene, butene and isobutene having molecular weights of up to 5000. One such advantageous olefin is a $C_{30}$ terminal monoolefin having a melting point of 30°–40° C. Internal monoolefins may also be used, but preferably no higher than 2-olefin and 3-olefin types.

With respect to the carboxylic acid used in preparing the lactams of this invention, suitable reactants include acetic, propionic, butyric, pentanoic, hexanoic and heptanoic acids and their isomers. Acetic acid is the preferred reactant.

A preferred method of producing the latter is from a carboxylic acid solution of the metal ion, e.g. an acetic acid solution of manganic acetate. The solution is heated to temperatures up to the boiling point, or even above the boiling point when pressure is used. It is understood that a transient free radical is probably generated via hydrogen loss from a molecule of the acid which acts as a ligand to $Mn^{+3}$.

Other useful methods for producing carboxymethyl free radicals are described in application Ser. No. 714,447.

Other free radicals, corresponding to the formula,

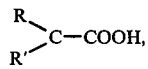

may be generated from manganic ions and an acid, e.g. propionic, butanoic, pentanoic and the like. In each case, the acid has at least one alpha hydrogen atom. With propionic acid, the free radical is methylcarboxymethyl, $CH_3\dot{C}HCOOH$; with butanoic acid, it is ethylcarboxymethyl, $CH_3CH_2\dot{C}HCOOH$; and with methylpropionic acid it is dimethylcarboxymethyl, $CH_3(CH_3)\dot{C}COOH$. In the foregoing free radical preparations, the manganic salts could include propionate, butyrate, isobutyrate and hexanoate (caproate).

The preferred metal ion for use in the process for forming the lactones is trivalent manganese, or manganic ion, $Mn^{+3}$, which is reducible to bivalent manganese, or manganous ion, $Mn^{+2}$. Manganic acetate dihydrate is a preferred $Mn^{+3}$-producing compound. Cerium is also a useful metal in this invention.

The solvent for the reacting monoolefin and the manganese compound, or other metal compound, is preferably an alphahydrogen-containing aliphatic carboxylic acid, in excess quantities of the acid used in the reaction is satisfactory. As stated, acetic acid is the preferred reactant-solvent. Other suitable solvents and details in the process for forming the lactones are made available in said abandoned application Ser. No. 714,447.

As theorized, the olefin is simply admixed with the metal carboxylate in the presence of excess carboxylic acid and the temperature is increased to 150° to 250° C. The following simplified sequence is understood to occur:

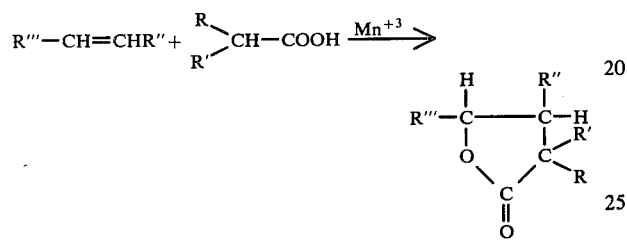

If the olefin is a terminal olefin (R″=hydrogen) only the gamma carbon is substituted. When acetic acid is used (R and R′=hydrogen) there is no alpha substitution. Straight chain acids of 3 or more carbon atoms furnish mono-alpha substitution; 2,2-disubstituted acids result in di-alpha sustitution. R‴ contains at least 16 carbon atoms in length, and preferably has a total carbon atom content of at least 25. Excess branching is undesirable for reasons of solubility, performance and ease of biodegradability which may be important under certain uses.

The lactones so produced have utility in increasing the adherent properties of wax to paper by hot melt technique. Moreover, in hydrocarbon fluid, they provide unexpected antiwear properties.

Upon reaction of the lactones of this invention with tetraethylene pentamine and similar polyalkylene polyamines of the formula $H_2N-(C_nH_{2n}NH)_m-H$, wherein n is an integer of 2 to 4 and m is an integer of from 1 to 10, and the removal of water, lactams or bislactams may be produced. Reaction with the amine is believed to open the lactone ring. However, the removal of water closes the ring again wherein the cyclic oxygen atom has been replaced by the basic nitrogen atom of amine. Accordingly, reactions of 1:1 to 2:1 of lactone to amine provide useful longchain lactam and bislactam products useful in organic fluids as detergents and antioxidants. Ethylenepolyamines are preferred.

For the purpose of providing such additive properties, it has been found that polymeric olefins of propylene and butene and the like are most suitable. Polyolefins of molecular weights ranging up to 5000 may be used, and preferably up to about 2000 (about 140 carbon atoms).

The lactones may also be reacted with mono-amines to provide useful products. For example, a butene or isobutene polymer containing about 90 carbon atoms and having terminal unsaturation is reacted with manganic acetate to form the lactone,

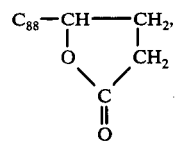

then reacting this with an amine, $R_aNH_2$, to form products like

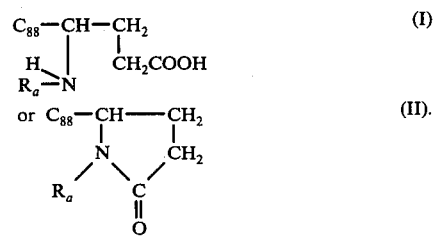

By further treatment of (I) with an amine, $R_aNH_2$, there may be formed

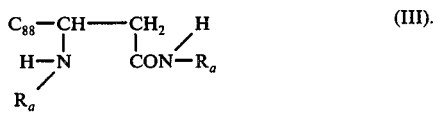

Compounds (II) and (III) are also useful as antioxidants. $R_a$ is alkyl or aryl of from 1 to about 20 carbon atoms.

The following examples serve to illustrate and in no sense limit the invention. All parts are by weight unless otherwise specified.

A. PREPARATION OF LACTONES

EXAMPLE 1

A four-neck, five liter flash equipped with a stirrer, thermometer, $N_2$ inlet and a condenser, is charged with 2800 grams of glacial acetic acid and 1200 grams of potassium acetate. The resulting mixture is heated to reflux. A quantity, 210 grams or approximately 0.5 mole, of the $C_{30}$ terminal olefin described above, and 283.5 grams of manganic acetate dihydrate are added to the mixture. After one hour of heating at reflux, a clear solution is obtained. An additional 283.5 grams of the manganic acetate is added, and refluxing is continued for an additional hour, whereupon a clear solution is obtained. The solution is cooled to about 20° C. and is diluted with 5 volumes of water. A waxy layer containing the lactone product forms on top of an aqueous layer and is decanted.

Ethanol (1000 ml) and 50 grams of potassium hydroxide dissolved in 400 ml of water are added to the waxy layer, whereupon the potassium salt of the lactone is formed. The reaction mixture is refluxed for one hour. An additional liter of water is added to the mixture, which is then extracted with carbon tetrachloride (1000 ml) to remove unreacted olefin. The aqueous layer and $CCl_4$ layer which are formed are separated. The aqueous layer is acidified with HCl (12N, 100 ml), whereupon the lactone is reformed. The acidified layer is extracted with toluene (500 ml). An aqueous layer and a toluene layer which are formed are separated. The toluene layer is distilled to remove solvents and water, and is concentrated on a rotovac. A light brown product (115.6 grams) is recovered. Infrared analysis reveals 8 percent of olefin present in the product, and vapor phase chromatography indicates a 7% olefin content. The melting point of the product is 35°–50° C.

EXAMPLE 2

Using similar equipment and procedure as that of Example 1, 1-octadecene is reacted with manganic acetate dihydrate in the presence of excess acetic acid. The resulting reaction mixture is separated as in Example 1 in which the organic phase contains gamma-hexadecyl-gamma-butyrolactone.

EXAMPLE 3

Using equipment and reaction conditions similar to that of Example 1, a 1-polybutene having a molecular weight of about 830 is reacted with manganic acetate in the presence of acetic acid. The reaction product is separated in the same manner as in Example 1 except potassium hydroxide is not used. The organic phase is separated from the aqueous phase by use of water washes and interfacial separations. The organic phase contains the corresponding gamma-polybutenyl-gamma-butyrolactone.

EXAMPLE 4

Using conditions similar to that of Example 3, a 1-polybutene of molecular weight of about 1380 is reacted with manganic acetate in the presence of acetic acid. After water washes and separations, the final organic phase contains the corresponding gamma-polybutenyl-gamma-butyrolactone.

B. REACTION OF LACTONES WITH AMINES

EXAMPLE 5

In a reaction vessel filled with a nitrogen inlet and thermometer, 62.1 grams (0.2 mole) of the lactone prepared in accordance with Example 2 is mixed with 18.9 grams (0.1 mole) of tetraethylenepentamine (for bis-lactams: 2:1 of lactone to amine). The reaction mixture is heated at 250° F. for 2 days under agitation with periodic nitrogen sweep to remove water vapor. Infrared tracking shows disappearance of the lactone absorption at 5.65 microns and appearance of the lactam absorption at about 6.1 microns. The viscous reaction mixture is mixed with hexane and activated charcoal; the charcoal is filtered out and the hexane removed by stripping under vacuum. The resulting product contains

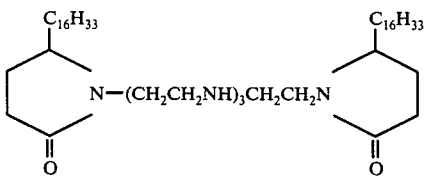

EXAMPLE 6

The lactone product of Example 3 and triethylenetetramine are reacted in a manner similar to that of Example 5, using a 2:1 mole ratio, except omitting the hexane-charcoal treatment. The reaction product contains

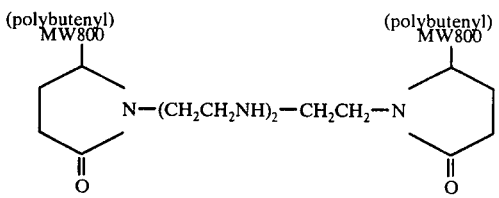

EXAMPLE 7

The lactone of Example 4 and triethylenetetramine are reacted in a manner similar to that of Example 6. The reaction product contains

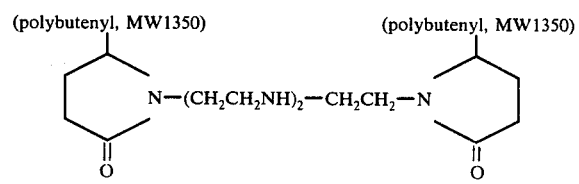

EVALUATION OF PRODUCTS

1. Antiwear Tests

Three 52-100 steel half-inch diameter balls are held immovable in a ball cup. A fourth ball attached to a rotatable spindle is brought into contact with the three at a force of 40 kg. and rotated against them at a speed of 600 r.p.m. or 23.3 cm/second, for 30 minutes. The lubricant for the rotation is cetane containing 0.1% by weight of a lactone. The ball cup and lubricant is held at 200° F. during the test. This four-ball test is a known procedure described in U.S. Pat. No. 3,278,432. The lubricant rating is based on the diameter of the weld scar (WSD) on the balls (in mm.) and the wear rate (in cc/cm × 10 inches). The lactones of Examples 1 and 2 are evaluated in this test since they are the only additives in the lubricant fluid. Other lactones of lower carbon-atom normal olefins are also tested; the heading "R" indicates the number of carbon atoms or, if none, hydrogen, in the gamma position. The results are:

| R | WSD | Wear Rate |
| --- | --- | --- |
| No additive | 0.775 | 12.2 and 10.5 |
| 0 | 0.815 | 15.5 |
| 1 | 0.838 | 17.4 |
| 6 | 0.766 | 12.0 |
| 8 | 0.735 | 10.0 |
| 10 | 0.756 | 11.3 |
| 14 | 0.804 | 14.7 |
| Example 2 | 0.718 | 9.1 |
| Example 1 | 0.674 | 7.0 |

The reduced wear of the steel in the last two results indicate the unexpected properties of the long chain gamma-substituted-gamma lactones of this invention.

The lactone of Example 2 is reacted with triethylenetetramine in the same manner as in Example 5. The bis-lactam product is added to a kerosene jet fuel, JP-7 which meets U.S. Mil. Spec. MIL-T-38219, at a concentration of 50 ppm. This composition is submitted to the pin-on-disk wear test described in detail in U.S. Pat. No. 3,554,908. In this test, the force is 4 kg; the apparatus is run at 46 cm/second at 125° F. for 3 hours. The same ratings as in the previous four-ball test are used. The jet fuel is also tested without additive. The results are:

| Additive | WSD | Wear Rate |
| --- | --- | --- |
| None | 2.769 | 550 |
| Bis-Lactam | 1.524 | 17.1 |

2. Antioxidant Tests

In this series of tests, a solvent refined mineral oil of 100 SUS at 100° F. and 0° F. pour point, containing 1% by weight of the bis-lactams of this invention, is subjected to oxidation at 175° C. by the following procedure: Into a vessel containing 30 grams of the oil composition oxygen is circulated at 5 liters per hour through a solenoid valve, in which the rate of oxygen absorption is measured. The time in hours which 1 mole of oxygen per kilogram of oil is absorbed by the oil is obtained; the longer the time the more resistant the oil composition. Also measured is the amount in grams of deposit caused by the oxidation during the oxidation period; the deposit is washed in hexane before being weighed. A test similar to that used here is described in U.S. Pat. No. 3,554,945. The bis-lactams tested are the products of Examples 5, 6 and 7. As a comparison the oil alone and the bis-lactam of gamma-octyl-gamma-butyrolactone and triethylenetetramine are tested. The results are:

| Additive | Absorption Time, hrs. | Deposit, grams |
| --- | --- | --- |
| None | 20.0 | 0.234 |
| Octyl-group | 28.6 | 0.4258 |
| Example 5 | 40.1 | 0.4493 |
| Example 6 | 40.4 | 0.2755 |
| Example 7 | 35.6 | 0.3813 |

The comparison additive in 1% concentration extends the unit oxygen abosrption time only 8 hours, while the products of this invention extend it 15 to 20 hours. Another comparison additive, a bis-polybutenylsuccinimide of tetraethylenepentamine, in which the polybutene used in preparation has a molecular weight of about 900, also in 1% concentration, extends the unit absorption time to only 32.8 hours.

A mixture of 0.5% by weight of the product of Example 5 and 0.5% by weight of the said succinimide in the same oil is tested in the oxidation test. The unit absorption time is 42.6 hours.

It will be seen that the lactones and their amine derivatives in accordance with this invention are useful agents in industrial organic fluids such as lubricants, fuels, greases and the like. They may be used alone or in conjunction with other additives, such as the polyalkenylsuccinimides.

Mixed lactones are various alkyl carbon atom lengths may also be used, as shown in Example 8.

EXAMPLE 8

A mixture of $C_{15}$ to $C_{20}$ 1-olefins is reacted with manganic acetate in the presence of acetic acid as described in Example 1, except that the manganic acetate is prepared in situ by adding potassium permanganate in sufficient amount to produce conversion to the higher oxidation level. The average chain length of the olefin is about 17. The resulting lactone product is separated and 118.6 grams is mixed with 35.1 grams of triethylenetetramine in a manner similar to Example 5. Some water is distilled off to permit the temperature to reach 250° F.

Aspects of this invention have been described in narrow terms, however all modifications thereof which would be obvious are considered to be within the scope of this invention, as claimed in the following claims:

What is claimed is:
1. A compound having the structure:

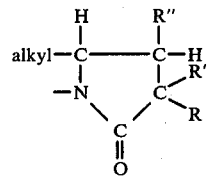

wherein the alkyl group has from 16 to 100 carbon atoms; R, R' are R" are individually selected from the group consisting of hydrogen, methyl and ethyl; and —N is the amino nitrogen of a lactam polyamine having the structure

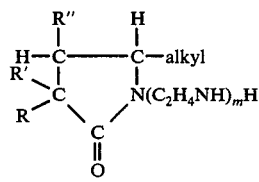

wherein $m$ is an integer of 1 to 10 and R, R' and R" are individually selected as previously defined.

2. The compound of claim 1 wherein both R and R' are hydrogen.
3. The compound of claim 1 wherein said alkyl group is derived from propylene or butene polymer and R" is hydrogen.
4. The compound of claim 1 wherein said alkyl group contains at least 16 carbon atoms in a straight chain.
5. The compound of claim 1 wherein $m$ is 3 or 4.
6. A bis-lactam obtained from a gamma-alkyl-gamma-butyrolactone of the formula

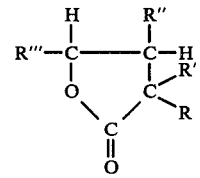

wherein R, R' and R" are individually selected from the group consisting of hydrogen, methyl and ethyl, and R''' is alkyl having a chain length of 16 to 100 carbon atoms, by reacting said butyrolactone with $H_2N(C_2H_4NH)_m$—H wherein $m$ is an integer of 1 to 10.

7. The bis-lactam of claim 6 having the structure

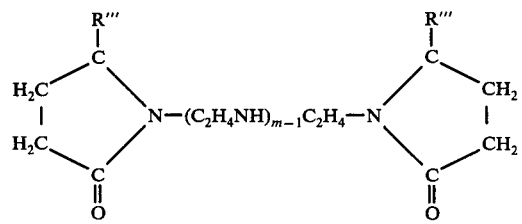

wherein R''' and $m$ are as defined.

8. The bis-lactam of claim 6 wherein R''' has a molecular weight of about 800 and $m$ is from 3 to 4.
9. The bis-lactam of claim 6 wherein R''' has a molecular weight of about 1350 and $m$ is from 3 to 4.
10. The bis-lactam of claim 6 wherein said amine is tetraethylenepentamine and both R and R' are hydrogens.

* * * * *